United States Patent [19]
Salomon et al.

[11] Patent Number: 5,854,399
[45] Date of Patent: Dec. 29, 1998

[54] ANTIBODIES SPECIFIC FOR HUMAN CRIPTO-RELATED POLYPEPTIDE CR-3

[75] Inventors: David S. Salomon, Germantown, Md.; Maria G. Persica, Naples, Italy

[73] Assignee: The United States of America as represented by the Department of Health and Human Services, Washington, D.C.

[21] Appl. No.: 464,023

[22] Filed: Jun. 5, 1995

Related U.S. Application Data

[62] Division of Ser. No. 154,198, Nov. 17, 1993, Pat. No. 5,620,866, which is a division of Ser. No. 749,001, Aug. 23, 1991, Pat. No. 5,264,557.

[51] Int. Cl.⁶ .................................................. A61K 39/395
[52] U.S. Cl. ..................... 530/387.7; 530/389.7; 424/138.1; 424/139.1; 424/155.1; 424/174.1
[58] Field of Search .................. 435/7.1, 70.21, 435/172.2, 240.27; 424/138.1, 139.1, 155.1, 174.1; 530/387.7, 389.7

[56] References Cited

PUBLICATIONS

Ciccodicola, Alfredo, et al. (1989) "Molecular characterization of a gene of the 'EGF family' expressed in undifferentiated human NTERA2 teratocarcinoma cells", *The EMBO Journal*, 8:1987–1991.
Romkes et al. Biochemistry vol. 30:3247–3255 1991.

*Primary Examiner*—Sheela Huff
*Assistant Examiner*—Julie E. Reeves
*Attorney, Agent, or Firm*—Townsend & Townsend & Crew

[57] ABSTRACT

The present invention relates, in general, to a human CRIPTO-related gene. In particular, the present invention relates to a DNA segment encoding a human CRIPTO-related gene; polypeptides encoded by said DNA segment; recombinant DNA molecules containing the DNA segment; cells containing the recombinant DNA molecule; a method of producing a human CRIPTO-related polypeptide; a DNA segment encoding a genomic clone of the human CRIPTO gene (CR-1); antibodies specific to CR-3; and a method of measuring the amount of CR-3 in a sample.

2 Claims, 13 Drawing Sheets

```
CR-1  →   GCCGGCACTCCCACTGGAGAGTCCCAGCTGCCTCTGGCCG CCCCTCCCCTCTCCC GGGCAC

CR-3  →   AAGCTTGCGCGCCATGTAAGGTAAAGTGACTGATTCTATAGCAATCCAATTGTTCCTTGTCTGCCCGTTTACATATAACAA
          CTGGGCGCCGCTCCCGCGTCCCTTTCAGGAATTCAGTCCGCCTGGAATTGCACTTCAAGTCTGGAGCCCCAAGGAACCCCTCCTGACCCTGA

TGTTGTCAATGTTTGATTGAAAAATACCTAGCAGGTG
          ACTTCTATCTCAGTTCCTAGTGTTCCCCACACACACACACCTAGTCTCCTCAGGCGGAGAGCA CCCCTTTCTT GGCCACCCGGGTATCC
                                                                      C
                                                                      ∨
                             T   G  ΔΔ  Δ
          CCCAGGGAGTACGGGGCTCAAACACCCTTCTGGAAAAACAAGGTGAAGCAAATTTCAGAAGTAAAACTTCTGAAATAAAATAAAATATCGA
                                                                                            G
          ATGCCTTGAGACCCATACATTTTCAGGTTTTTCCTAATTAAAGCAATTACTTTCCACCACCCCTCCAACCTGGAATCACCAACTTGATTAGAGAAAC
                                    Δ                                 A
          TGA TTTTTCTTTTTTCTTTTTTTTCCC GAAAAGAGTACCCTCTGATCATTTTAGCCTGCAACTAATGATAGAGATATTAGGGCTAGTTAACCACAG
                      Δ
          TTTTACAAGA CTCCCTCTTCCC GCGTGTGGGCGCCATTGTCATGCTGTCGGT CCCGCC CACCTGAAAGGTCTC CCCGCC CCGACTGGGGTTTGTGTT
                                                                                                    A
          GAAGAAGGAGAATCCCCGGAAAGGCTGAGTCTCCAGCTCAAGGTCAAAACGTCAAGGCCGAAAGCCCTCCAGTTTCCCCTGGACGCCTTGCTCCT
                       CG                                                                               T
          GCTTCTGCTACGACCTTCTGGGGAAAACGAATTTCTCATTTTCTCTTAAATTGCCATTTTCGCTTTAGGAGAGAATGTTTTCCTTTGGCTGTTT
                         Δ
          TGGCAATGACTCTGAATTAAAGCGATGCTAACGCCCTCTTTCCCCCTAATTGTTAAAAGCTATGGACTGCAGGAAGATGCCGCTTCCTTACAG
                                                               +1         M  D  C  R  K  M  A  R  F  S  Y  S
                                                                                        V
```

FIG. 2A.

IVS1
•---
GTATGAGCTAATCTTAGAATAGTGAACTTTTTTTGATTGCTAGAGATTGCCAGCTTAGGAAGTAATGTTCTACACTGTCATTTGATTTTCTCCTT
GCTCAAGCCCTAAAAGAGCTGCCAACCGACTGCTGTTTTTCCTGAAAGACCTGGAATTCACATGGTTACTTCTAACTTTGCCATTGGCTTTTAAC
ATTTCGTGTTAATGTTAATTTTCATTTTATGTTAATGACTCTGCCTATGAAATAGTGTTTCTTTACTTCTTGTACAAATAAGGTCAGTACTACA
ACCAAATTTAAATCTTCCGAAAGATTAAAGGTATAAGCAGATTCAATACTTGGCAAAACTATTAAGATAATAGCAAAAAAAAAAAAAACCCAC
ATTTTTTACCTAAAAACCTTTTAAGTGATTGGTTAAAATAGTTTGGCCGGGTGCGGTGGCTCACGCCTGTAATCCTAGCACTTTGGGAGGCAGAGG
CGGGTGGATCACTGAGGTCAGGAGACCAGCCTGGCCAACATGGCAAACCCCGTCTCTATTAAAAATACAAAAATTAGCCAAGCATGGTGGCGGGC
ACCTGTAATCCCAGCTACTCTGGAGGCTGAGGCAGGAGAATTGCTTGAACTGGGAGGCAGGAGGNCAGTGAGCCGAGATCGCACCATTGCACTCCAG
CCTGGGTGAAAACCGAAACTCCCCTCTCAAAAATAAATAAATAAATACAGTAGTTTGTAAAATGATTCATCGGTAACATGGATGCAGCTATTTT
TAATCCTTATGAAATTGTATGCAGGGGAAAACATGTGAAATAGAAGACATATACCTACTTAAAATTAGGTACTTATGTGAGGACAG
GGCCTAAGAATAATAATAATATATTAAAAAGACTTGGATATTGGTGACTTTTTTTCAACATTTTTCTTGTTACATGAATTAGCCATTAAAAAAAG
AAAGATGGTGCTCTACAATTCTTTTCAGTGATCTGTGGTCTTGTCCTTGTGATGAGAGACCTGGGTGTTAACTTGTAAGGTTTTATTTCCTTTG
TTTGGCTAACTCATGTTTGACTTCCTCTTC

IVS1
---•
CTAGTGTGATTGGATCATGGCCATTTCTAAAGTCTTTGAACTGGATTAGTTGCGGTGAGAGACCTTTTGTTCTTTTGATCACTCTCAATTTTA
   V  I  W  I  M  A  I  S  K  V  F  E  L  G  L  V  A
                          C
                                 IVS2
                                 •---

```
                                                                                          IVS4
                                                                                          ···●
TCAGAGGGGGGGGGAGCCGTGGAGAGGAGAGAAAGGGAAGTGGAAATTTCAGACCCAAGCTATCGCAGCTTACCTGTTCATTCTCAGGAACTGT
                    E                                                                     N  C

GGGTCTGTGCCCCATGACACCTGGCTGCCCAAGAAGTGTTCCCTGTGTAAATGCTGGCACGGTCAGCTCCGCTGCTTCCTCAGGCATTTCTACCC
 G  S  V  P  H  D  T  W  L  P  K  K  C  S  L  C  K  C  W  H  G  Q  L  R  C  F  P  Q  A  F  L  P
    IVS5
    ●···
GGCTGGTAAGCGGAGGTTCCCTCTTTCTTTTGCCCTTTGAAGTTACGTAGTTGCCTTGGGGGGTGCTTAGTTAGCAGGCTCTCCTTGTACC
 G  C

TCTTGTCTTGCTAGAGCCTGGCAGCCAAAGTTCTGCTTATAAAGCATCGCAGACTCCTGATGAGATAGTTGCCTTGGCCTTCTTTGATATTTATTT
CCTCGGGAACCTGGCTAGTCCTGCTCCTGCCCTTCAGATAGAGATGTATTTCAAGTCTATTTGACATTTTATGTCTGAACTTCTATTGAGGAAATAA
ACAAGTCTCGGTCTCTCTTGTTAAACCAAGAGATGTTCTCTGGTGTTCCTTTCCTTGGGTAGGGGGACCCAAACCAGGATGGCAGCTCATTTAGA
GCCCACCCCTGACGACAAATTCTATCAGAGGCTTGGCCCCTGCCTAGTCCTTTAGAAACTTCCAGAGTCCTAAAGTCCCTGTAACCCCCCTCCCA
TACCTTACCATGACTGGTCACAGAACCCTTACCATGCTGGTCACAGAACCCTTTCACCTTCTTGATTTTTTACTGATTGAGGAATACAATGAAA
AGAAGGGCAGCACCTGGAGAGGAAAGAGGCGACAGTCCTCTCCCAGGAAGTAAATGAAGCAAACATTTCACTGAGAACAGGAAGGAATTCCCC
ATAGTTCTGGGCCTTGGAGATGTAGAATGTAGAAATATTCAAGCCCAGGAAGCTCAGGTGTCAGGCTCAGGTGTCAGGATAGGTGTTTGATAAGTGTGGGTTGGGTGATTGGATGTGTAG
AATCCAGACAGGATTGTGTCTTTGCCATTTGCATCCGGGTGTCAGGCTCAGGTGTCATCCGGGTGTCAGGATAGGTGTTTGATAAGTGTGGGTTGGGTGATTGGATGTGTAG
GGAACATTTGCTCTTCCTGGAACATGGGCCCAAGTCAGAATCTAACCCAGGTGTGTCTGCTCATTCCTGCAAGTGAAGGCATCACCACTGGGCTAGGT
TCCAGGTGTGAGTGTCCTGAGAAGAGCAGGTTCACAGTAGCGTATAGATATGCCACATTTGTGGGCAGCAGGATGAACTGCCAGAGAGGTTTGCTT

```
                    CAC                     G
GAATTATATGTTCAGATTATTGGAGACTAATTCTAATGTGGACCCTTAGAATACAGTTTTGAGTAGAGTTGATCAAAATCAATTAAAATAGTCTCTT

TAAAGGAAAGAAACATCTTTAAGGGGAGGAACCAGAGTGCTGAAGGAATGAAGTCCATCTGCGTGTGTGCAGGGAGACTGGGTAGGAAAGAGGA

AGCAAATAGAAGAGAGAGGTTGAAAAACAAAATGGGTTACTTGATTGGTGATTAGGTGGTGGTAGAGAAGCAAGTAAAAGGCTAAATGGAAGGGC
                            G           G                T
AAGTTTCCATCATCTATAGAAAGCTATATAAGACAAGAACTCCCCTTTTTTCCCAAAGGCATTATAAAAGAATGAAGCCTCCTTAGAAAAAAAA
                                                                  G
ATTATACCTCAATGTCCCCAACAAGATTGCTTAATAAATTGTGTTTCCTCCAAGCTATTCAATTCTTTTAACTGTTGTAGAAGACAAAATGTTCAC

AATATATTAGTTGTAAACCAAGTGATCAAACTACATATTGTAAAGCCCCATTTTTAAAATACATTGTATATATGTGTATGCAC AGTAAA AATGAAA

AAAAAAAAAAGGAAACCACCCCTTAGGCAGGCAGGACATGCTCTTCAGAACTCTCTGCTCTTCAGAGTTCCAAAGAAGGGATAA
         AAAAAAAAAAGGAAACCACCCCTTAGGCAGGCAGGACATGCTCTTCAGAACTCTCTGCTCTTCAGAGTTCCAAAGAAGGGATAA
CTATATTGACCTAAATGTGAACTGGTTATTCTAGGTGCTTAGGTGGTGAGGTGCTTATGGTGGTGGTTTGCTCTGATGCCCTTTTTGCATTTTCCAAA

AACATCTTTTAT  -  CR-3
GTACCATGGTGAGGATGTGTTATATCTTTTCCAGGGTCCTAAAAGTCCCTGCAACTCCCTGCCCCATACCCTACCATGACTGGTCACAGAACCCTTT
```

FIG. 2F.

CACCTTATTGTACTGATTTCATATGGAATATGGCAACTACATCTGGCTCAAAACAAAGGAAACCAGAAGAGCCAAGTCCCAGGTGAGTGCTC

AGTTCTGTTTCTAGCTTTGACGTGTGTCTTCTCTGTGAAGGACAAAATTGCTTCTATTATTTAGGTACCATAATTTGTGTTTTTCCAAATTAATT

CCCTGCAG — CR — 1

FIG. 2G

… # ANTIBODIES SPECIFIC FOR HUMAN CRIPTO-RELATED POLYPEPTIDE CR-3

This application is a division of application Ser. No. 08/154,198, filed Nov. 17, 1993, now U.S. Pat. No. 5,620,866 which is a division of application Ser. No. 07/749,001, filed Aug. 23, 1991, now U.S. Pat. No. 5,264,557, all of which are hereby incorporated in their entirety by reference.

BACKGROUND OF THE INVENTION

1. Field of the Invention

The present invention relates, in general, to a human CRIPTO-related gene. In particular, the present invention relates to a DNA segment encoding a human CRIPTO-related gene; polypeptides encoded by the DNA segment; recombinant DNA molecules containing the DNA segment; cells containing the recombinant DNA molecule; a method of producing a human CRIPTO-related polypeptide; a DNA segment encoding a genomic clone of the human CRIPTO gene (CR-1); antibodies specific to CR-3; and a method of measuring the amount of CR-3 in a sample.

2. Background Information

Polypeptide growth factors play a role in stimulating cell proliferation. Their genes are expressed in the developing embryo, in normal adult tissues and in tumor cells (for review see Devel, T. F., Ann. Rev. Cell Biol. (1987) 3:443–492; Sporn, M. B. et al., Nature (1987) 332:217–219; Whitman, M. et al., Ann. Rev. Biol. (1989) 5:93–117). Characterization of these factors and sequencing of their genes have permitted their grouping into a relatively small number of families on the basis of sequence similarities (Mercola, M. et al., Development (1988) 108:451–460). One of these is the epidermal growth factor (EGF) family. EGF (Savage, C. R. et al., J. Biol. Chem. (1972) 247:7612–7621), transforming growth factor α (TGFα) (Derynck, R. et al., Cell (1984) 38:287–297) and amphiregulin (AR) (Plowman, G. D. et al., Mol. Cell Biol., (1990) 10:1969–1981) share structural similarities including the conservation of six cysteines of the "EGF motif", which in EGF are involved in three disulfide bonds defining the tertiary structure. The presence of "EGF motif" also in developmental genes, such as Notch in Drosophila (Kidd, S. et al., Mol. Cell. Biol. (1986) 6:3094–3108) and lin-12 in C. elegans (Greenwald, I., Cell (1985) 43:583–590), may imply a novel role for the growth factors of the "EGF family." It has been suggested that they may exert their action on the cell surface during development to mediate cell-cell interactions by recognizing a complementary receptor on another cell.

Previously, the isolation of a human cDNA, referred to as CRIPTO (CR-1) (Ciccodicola, A. et al., EMBO J. (1989) 8:1987–1991), encoding a protein of 188 amino acids was described. The central portion of this protein shares structural similarities with the human TGFα (Derynck, R. et al., Cell (1984) 38:287–297), human AR (Plowman, G. D. et al., Mol. Cell Biol., (1990) 10:1969–1981) and human EGF (Savage, C. R. et al., J. Biol. Chem. (1972) 247:7612–7621). Northern blot analysis of a wide variety of tumor and normal cell lines and tissues (e.g., choriocarcinoma, fibroblast, neuroblastoma, HeLa, placenta and testis) has shown that CRIPTO transcripts are detected only in undifferentiated human NTERA-2 clone D1 (NT2/D1) and mouse (F9) teratocarcinoma cells and these disappear after inducing the cells to differentiate with retinoic acid treatment (Ciccodicola, A. et al., EMBO J. (1989) 8:1987–1991).

SUMMARY OF THE INVENTION

It is a general object of this invention to provide a human CRIPTO-related gene (CR-3).

It is a specific object of this invention to provide a DNA segment which encodes a human CRIPTO-related gene (CR-3).

It is a further object of the invention to provide a polypeptide corresponding to a human CRIPTO-related gene (CR-3).

It is another object of the invention to provide a recombinant DNA molecule comprising a vector and a DNA segment encoding a human CRIPTO-related gene (CR-3).

It is a further object of the invention to provide a cell that contains the above-described recombinant molecule.

It is another object of the invention to provide a method of producing a polypeptide encoding a human CRIPTO-related gene (CR-3).

It is a further object of the invention to provide a genomic DNA segment coding for a polypeptide comprising an amino acid sequence corresponding to a human CRIPTO gene (CR-1).

It is a further object of the invention to provide antibodies having binding affinity to a human CRIPTO-related gene (CR-3), or a unique portion thereof and not to CR-1, or a unique portion thereof.

It is a further object of the invention to provide a method of measuring the amount of CR-3 in a sample.

Further objects and advantages of the present invention will be clear from the description that follows.

In one embodiment, the present invention relates to a DNA segment coding for a polypeptide comprising an amino acid sequence corresponding to a human CRIPTO-related gene CR-3.

In another embodiment, the present invention relates to a polypeptide free of proteins with which it is naturally associated and comprising an amino acid sequence corresponding to a human CRIPTO-related gene (CR-3).

In a further embodiment, the present invention relates to a recombinant DNA molecule comprising a vector and a DNA segment that codes for a polypeptide comprising an amino acid sequence corresponding to a human CRIPTO-related gene (CR-3).

In yet another embodiment, the present invention relates to a cell that contains the above-described recombinant DNA molecule.

In a further embodiment, the present invention relates to a method of producing a polypeptide comprising an amino acid sequence corresponding to a human CRIPTO-related gene (CR-3).

In another embodiment, the present invention relates to a genomic DNA segment coding for a polypeptide comprising an amino acid sequence corresponding to a human CRIPTO gene (CR-1).

In yet another embodiment, the present invention relates to an antibody having binding affinity to a human CRIPTO-related gene (CR-3), or a unique portion thereof and not to CR-1, or a unique portion thereof.

In a further embodiment, the present invention relates to a method of measuring the amount of CR-3 in a sample, comprising contacting the sample with the above-described antibodies and measuring the amount of immunocomplexes formed between the antibodies and any CR-3 in the sample.

BRIEF DESCRIPTION OF THE DRAWINGS

In FIG. 1A, 10 μg of genomic DNA was digested with EcoRI (E), PstI (P) and EcoRI+PstI (E/P), and size-fractionated by agarose gel electrophoresis. Hybridization probes are $^{32}$P-nick-translated 2B3 and G2 segments. The molecular weight markers included are HindIII/EcoRI-digested Lambda DNA. In FIG. 1B 10 μg of mouse (first three lanes from left) and chicken DNA (fourth and fifth lanes) was digested with PstI (P), BamHI (B) and EcoRI (E). Hybridization probe is $^{32}$P-nick-translated 2B3 segment. Electrophoresis, transfer and hybridization were as described below except for washing conditions (2×SSC at 60° C.).

FIG. 2. Nucleotide sequence of CR-1 and CR-3 genomic DNAs. The sequence of 5763 nucleotides of the CR-1 gene is shown. The nucleotides are numbered from the start codon and the amino acids for CR-1 are shown below. The nucleotide sequence of CR-3 is shown on top of CR-1. Nucleotide changes and deletions (Δ) in the CR-3 sequence are indicated above the CR-1 sequence. The six amino acid changes are indicated below the CR-1 protein sequence. It is to be noted that all the introns of CR-1 are absent in the CR-3 sequence. The boxed motifs are Spl binding sites (solid-line boxes), pyrimidine stretches (thin-line boxes) and polyadenylation signals (broken-line box). The vertical arrows indicate the multiple transcription starts. The Alu sequence present in the mRNA is underlined.

DETAILED DESCRIPTION OF THE INVENTION

Figure 1A:
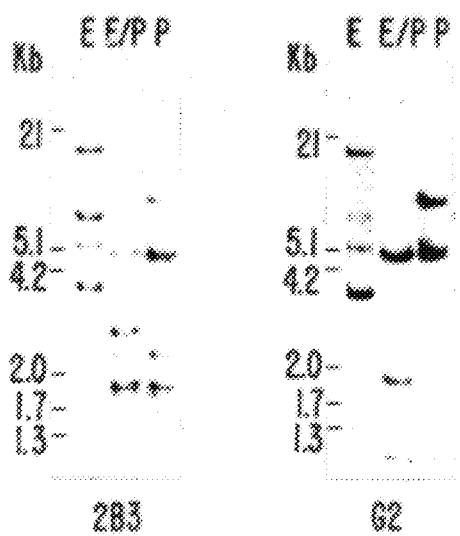
FIG. 1A, B and C. CRIPTO-related sequences in human and mouse DNA.

The present invention relates to a human CRITPO-related gene. This novel human gene (designated CR-3) has been isolated and cloned from a human genomic library using a human CRIPTO cDNA fragment. The CR-3 gene sequence is identical to the human CRIPTO gene sequence with the exception of eight base pair substitutions that give rise to six amino acid changes in the sequence of the protein. The CR-3 human cDNA has been expressed in mammalian COS cells and the recombinantly produced protein can be used to study its biological properties and as an immunogen to generate monospecific antibodies.

CR-3 exhibits partial amino acid sequence homology and a tertiary structure within a 38 amino acid region similar to the EGF supergene family that includes EGF, TGFα, and amphiregulin. Since those peptides are potent mitogens that are involved in regulating the proliferation, differentiation, and transformation of various mesenchymal and epithelial cells, CR-3 like CRIPTO can be expected to be a regulatory molecule that is involved in each of these processes. In addition, expression of CR-3 may serve as a tumor specific marker that may have applicability in the diagnosis, prognosis, and possible treatment of specific types of cancer. In this respect, CR-3 mRNA is expressed in several human colon cancer cell lines and possibly in human colorectal tumors.

In one embodiment, the present invention relates to DNA segment coding for a polypeptide comprising an amino acid sequence corresponding to a human CRIPTO-related gene (CR-3) and allelic and species variation thereof. In a preferred embodiment the DNA segment comprises the sequence shown in SEQ ID NO:4. In another preferred embodiment, the DNA segment encodes the amino acid sequence set forth in SEQ ID NO:5.

In another embodiment, the present invention relates to a polypeptide free of proteins with which it is naturally associated (or bound to a solid support) and comprising an amino acid sequence corresponding to a human CRIPTO-related gene (CR-3) and allelic and species variation thereof. In a preferred embodiment, the polypeptide comprises the amino acid sequence set forth in SEQ ID NO:5.

In another embodiment, the present invention relates to a recombinant DNA molecule comprising a vector (for example plasmid or viral vector) and a DNA segment coding for a polypeptide corresponding to CR-3, as described above. In a preferred embodiment, the encoding segment is present in the vector operably linked to a promoter.

In a further embodiment, the present invention relates to a cell containing the above described recombinant DNA molecule. Suitable host cells include procaryotes (such as bacteria, including E. coli) and both lower eucaryotes (for example yeast) and higher eucaryotes (for example, mammalian cells). Introduction of the recombinant molecule into the cell can be effected using methods known in the art.

In another embodiment, the present invention relates to a method of producing a polypeptide having an amino acid sequence corresponding to CR-3 comprising culturing the above-described cell under conditions such that the DNA segment is expressed and the polypeptide thereby produced and isolating the polypeptide.

In a further embodiment, the present invention relates to a DNA segment coding for a polypeptide comprising an amino acid sequence corresponding to a human CRIPTO gene (CR-1) wherein said DNA segment comprises the sequence shown in SEQ ID NO:2. The CR-1 genomic clone can be used in transgenic animals to examine the effects of overexpression of this gene on development and tumorigenicity and to study the regulation of this gene via sequences in the 5'-flanking region that are upstream from the ATG translation initiation codon.

In yet another embodiment, the present invention relates to an antibody having binding affinity to a human CRIPTO-related gene (CR-3), or a unique portion thereof and not to CR-1, or a unique portion thereof. In one preferred embodiment, CR-3 has the amino acid sequence set forth in SEQ ID NO:5, or allelic or species variation thereof.

Antibodies can be raised to CR-3, or unique portions thereof, in its naturally occuring form and in its recombinant form. Additionally, antibodies can be raised to CR-3 in both its active form and inactive form, the difference being that antibodies to the active CR-3 are more likely to recognize epitopes which are only present in the active CR-3.

CR-3 may be joined to other materials, particularly polypeptides, as fused or covalently joined polypeptides to be used as immunogens. CR-3 or its fragments may be fused or covalently linked to a variety of immunogens, such as keyhole limpet hemocyanin, bovine serum albumin, tetanus toxoid, etc. See for example, Microbiology, Hoeber Medical Division (Harper and Row, 1969), Landsteiner, Specificity of Serological Reactions (Dover Publications, New York, 1962) and Williams et al., Methods in Immunology and Immunochemistry, Vol. 1 (Academic Press, New York, 1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., editors, Basic and Clinical Immunology, (Lange Medical Publications, Los Altos, Calif., Fourth edition) and references cited therein, and in particular in Kohler and Milstein in Nature 256:495–497 (1975), which discusses one method of generating monoclonal antibodies.

Antibodies having binding affinity to a human CRIPTO-related gene (CR-3), or a unique portion thereof and not to CR-1, or a unique portion thereof can be isolated using screening methods (for example, ELISA assays). Antibodies having binding affinity for CR-3 (with or without binding affinity for CR-1) can be used in immunoassays to detect CR-3.

In a further embodiment, the present invention relates to a method of measuring the amount of CR-3 in a sample, comprising contacting the sample with the above-described antibodies and measuring the amount of immunocomplexes formed between the antibodies and any CR-3 in the sample. Measuring the amount of immunoclomexes formed can be any of those well known in the art, such as RIA, ELISA, and direct and indirect immunoassays.

EXAMPLES

The following protocols and experimental details are referenced in the Examples that follow:

Southern blot analysis and chromosomal mapping panels. All the hybrid cell lines were hamster x human obtained following a published protocol (Davidson, R. D., *Somatic Cell Gen.* (1976) 2:165–176). The hybrid clones were characterized for their human chromosome content (Rocchi, M. et al., *Hum. Gen.* (1986) 74:30–33).

DNA preparation from human peripheral blood lymphocytes and cell lines, restriction enzyme digestion, electrophoresis and Southern blotting were performed using standard techniques (Maniatis, T. et al., *Molecular cloning: A laboratory manual* (1982) Cold Spring Harbor Laboratory Press, NY). In general, 10 µg of DNA was digested with 40 units of enzyme. Electrophoresis of DNA digests was carried out in agarose gel (0.8%) in TEB buffer (89 mM Tris, 2 mM EDTA, 89 mM boric acid). DNAs were transferred by Southern capillary blot onto nylon membranes ZETABIND (AMF Cuno, Meriden, Conn.), fixed by UV cross-linking and hybridized to $10^7$ dpm DNA probes labeled by nick translation (Rigby, P. W. J. et al., *J. Mol. Biol.* (1977) 113:237–251) to a specific activity of about $2 \times 10^8$ dpm/µg. Washing was carried out at 65° C. in 2×SSC, 0.2% SDS and subsequently in 0.2×SSC, 0.2% SDS at 65° C.

Isolation of CRIPTO genomic clones. Genomic clones were isolated from two different human genomic libraries: one obtained by partial MboI digestion of genomic DNA cloned in the BamHI site of the pcos2EMBL. Cosmid Vector (Poustka, A. et al., *Proc. Natl. Acad. Sci. USA* (1984), 81:4129–4133), the other obtained by partial MboI digestion of genomic DNA that had been flush ended and cloned into the flush ended XhoI site of Lambda Fix Vector (Stratagene). $5 \times 10^5$ cosmids and $10^6$ phages were screened using the CRIPTO cDNA fragment 2B3 (see FIG. 1C) by standard techniques (Grunstein, M. et al., *Proc. Natl. Acad. Sci. USA* (1975) 72:3961–3965; Benton, W. et al., *Science* (1977) 196:180–182, respectively). The positive clones were analyzed by restriction mapping and the genomic fragments hybridizing to the human cDNA were subcloned in pUC18 Vector (Yanish-Perron, C. et al., *Gene* (1985) 33:103–109) or in pGEM-1 Vector (Promega). DNA sequencing of the genomic subclones was carried out using the modified dideoxynucleotide chain termination procedure (Hattori M. et al., *Nucl. Acids Res.* (1985) 13:78-13-7827). An oligonucleotide walking strategy was performed using synthetic 17-mer oligonucleotides (Applied Biosystems) deduced from the genomic sequence previously determined.

S1 nuclease mapping. Total RNA from undifferentiated teratocarcinoma cells NT2/D1 (Andrews, P. W. et al., *Lab, Invest.* (1984) 50:147–162) was isolated by cell lysis in 4M guanidine thiocyanate and sedimentation through 5.7M CsCl (Chirgwin, J. M. et al., *Biochemistry* (1979) 18:5294–5304). Poly(A)+ RNA was selected by chromatography on oligo(dT) cellulose (Aviv, H. et al., *Proc. Natl. Acad. Sci. USA* (1972) 69:1408–1412). 5 µg of poly(A)+ RNA or 40 µg of total RNA was hybridized with the 320 bp Sau96 fragment of Cr-1-73-H (FIG. 3), $^{32}$P-5'-end labeled, in 20 µl of 40 mM Pipes, pH 7, 0.4M NaCl, 1 mM EDTA, pH 7, and 80% formamide for 16 h at 50° C. Following hybridization, the reaction was diluted 10-fold with S1 nuclease buffer (0.28M NaCl, 0.05M sodium acetate, pH 4.5, 4.5 mM $ZnSO_4$ and 20 µg/ml single strand DNA). S1 nuclease (1200 units) was added and the reaction mixture was incubated for 2 h at 37° C. The reaction was terminated by the addition of 44 µl of termination buffer (2.5M ammonium acetate and 50 mM EDTA); the DNA:RNA hybrids were extracted with phenol, precipitated with ethanol, resuspended in sequencing dye, heated to 90° C. and resolved on a 6% acrylamide, 7M urea sequencing gel.

Primer extension. For primer extension analysis, a 35 bp synthetic oligonucleotide, ol GP2 (3'-CCCGGTAGAAGGACGTCAGGTATCGAAATTGTTAA-5') (SEQ ID NO:6) corresponding to base pairs −9 +21 of the first exon was end-labeled using T4 polynucleotide kinase to a specific activity of $10^8$ cpm/µg of poly(A)+ mRNA from NT2/D1 cells (Andrews, P. W. et al., *Lab. Invest.* (1984) 50:147–162) in a 40-µl volume containing 10 mM Pipes pH 6.4, 0.4M NaCl, 1 mM EDTA, by heating the reaction mixture for 3 min at 90° C., 2 min at 75° C. and gradual cooling to 42° C. After 14 h at 42° C., the resulting DNA:RNA hybrids were ethanol-precipitated and dissolved in reverse transcription buffer (50 mM Tris HCl pH 8, 0.1M KCl, 10 mM $MgCl_2$) in the presence of 500 µM deoxynucleotides and 20 units of reverse transcriptase. After 1 h at 42° C., the DNA:RNA hybrids were phenol-extracted, ethanol-precipitated, dissolved in sequencing dye, heated to 90° C. and resolved on a 6% acrylamide, 7M urea sequencing gel.

EXAMPLE 1

Genomic Complexity of CRIPTO Gene-Related Sequences in Human Chromosomes

The 2020 bp long CRIPTO cDNA previously described (Ciccodicola, A. et al., *EMBO J.* (1989) 8:1987–1991) contains an open reading frame of 564 bp, a 245 bp long 5' untranslated region, and a 1209 bp long 3' untranslated region that includes an Alu sequence element.

Figure 1B:
Figure 1C:
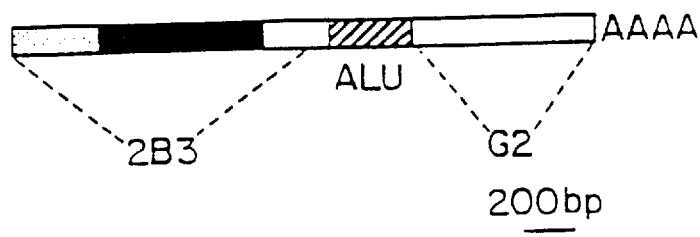
FIG. 1C shows a Schematic representation of human CRIPTO cDNA. The coding region is indicated by a solid box; AAAA indicates the poly(A) tail. cDNA regions corresponding to 2B3 and G2 probes are indicated.

As a first approach to characterize the genomic organization of the gene encoding the CRIPTO protein, Southern blot analyses were carried out. The two cDNA fragments, 2B3 and G2 (FIG. 1C), used as probes, hybridized to several genomic restriction fragments (FIG. 1A). The 2B3 probe, used to analyze by Southern blot the genomic DNA of mouse and chicken, hybridized to several bands in the lanes containing mouse DNA (FIG. 1B, first three lanes), whereas no hybridization was seen with chicken DNA (FIG. 1B fourth and fifth lanes).

EXAMPLE 2

Isolation and Characterization of CRIPTO Human Genomic Clones

To better understand the nature of the CRIPTO gene-related sequences, a human genomic library (Poustka, A. et al., *Proc. Natl. Acad. Sci. USA* (1984), 81:4129–4133) was screened using CRIPTO fragment 2B3 as a probe and 34 positive cosmid clones were isolated. EcoRI restriction analysis of 10 of the isolated clones revealed only 3 different restriction patterns in the inserts.

Figure 3:
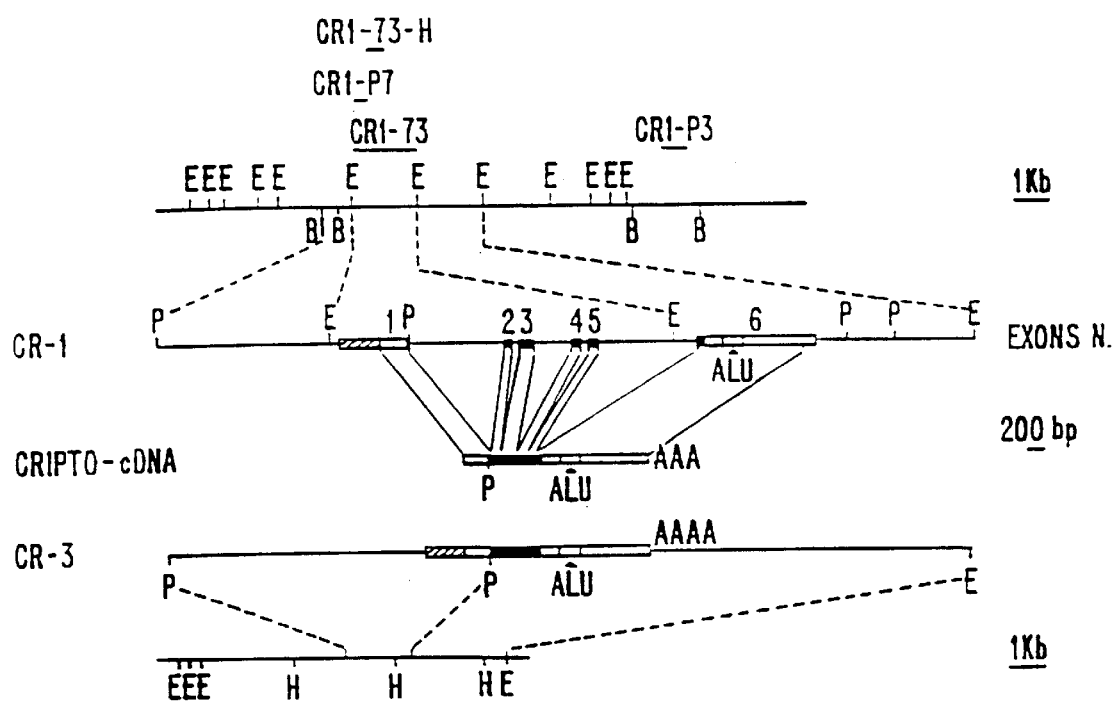
FIG. 3. Maps summarizing information obtained from DNA sequencing and restriction mapping of isolated CRIPTO homologous recombinant clones. Top: Physical map of CR-1. Numbered exons are indicated by black boxes for coding region and white boxes for non-coding regions. The hatched box represents the 440 bp upstream of the most common transcription start present also in CR-3. Restriction sites are indicated: EcoRI (E); BamHI (B); PstI (P). Thick lines above the map denote genomic subclones used as probes. Bottom: Physical map of CR-3. Below are represented the genomic region isolated and EcoRI (E), HindIII (H), PstI (P) restriction sites. CR-3 contains all the exons and a polyA tail (AAAA).

The isolated clones were hybridized to a synthetic oligonucleotide (G1) corresponding to nucleotides −91 to −110 of the 5' non-coding region of CRIPTO cDNA (Ciccodicola, A. et al., *EMBO J.* (1989) 8:1987–1991 and FIG. 2), with the intention of isolating the complete gene and discarding possible incomplete pseudogenes. A positive 800 bp PstI/EcoRI fragment (CR-1-P7) was identified in the CR-1 cosmid clone (FIG. 3 top).

DNA sequencing analysis revealed that clone CR-1 includes an intact structural gene encoding the entire human CRIPTO protein. The CRIPTO coding sequence is encoded by six exons spanning a 4.8 kb long DNA interval (FIG. 3 top). The nucleotide sequences at the exon-intron boundaries were established by DNA sequence comparison of cDNA and genomic subclones. The 5' donor and 3' acceptor splice sites in each of the five introns conform to the GT . . . AG rule and agree with the consensus sequence compiled for the exon-intron boundaries (Mount, S. M., *Nucl. Acids Res.*, (1982) 10:459–472) except for the acceptor sequence of the second and third introns (FIG. 2). Exon 1 is 281 bp in length and contains the initiator methionine. The other exons range in size from 52 to 1329 bp. The most 3' exon, 1329 bp in length, contains 118 bp of coding sequence and all of the 3' untranslated region (3' UT), which is 1209 nucleotides long (FIG. 2). The EGF-like domain exhibited by the CRIPTO protein (Ciccodicola et al. 1989) is encoded by exon 4.

A combination of S1 nuclease mapping and primer extension analyses was used to characterize the CR-1 transcription products.

Figure 4A:
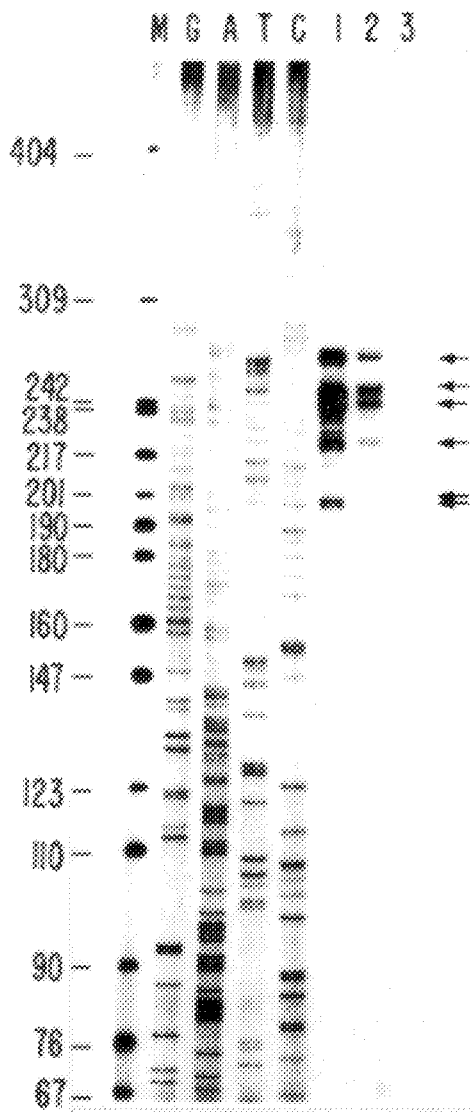
FIGS. 4A, 4B and 4C. S1 nuclease and primer extension analyses.

Since the CRIPTO gene was found to be expressed in an undifferentiated human teratocarcinoma cell line (NT2/D1) (Ciccodicola et al. 1989), poly (A)+ RNA isolated from cultured NT2/D1 cells was used. The probe used for S1 nuclease mapping was a double-strand DNA fragment encompassing nucleotides −302 to +18 of the genomic sequence and was labeled with $^{32}P$ at the 5' end (FIG. 4C). Five major S1 nuclease-protected fragments (FIG. 4A) mapping between positions −180 to −253 of the genomic sequence were observed (FIG. 4C).

Figure 4B:
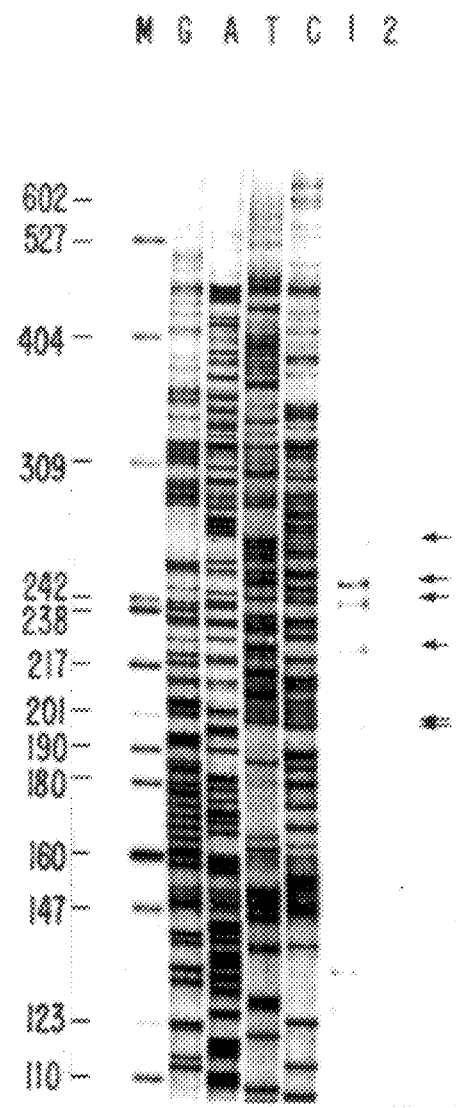
Figure 4C:
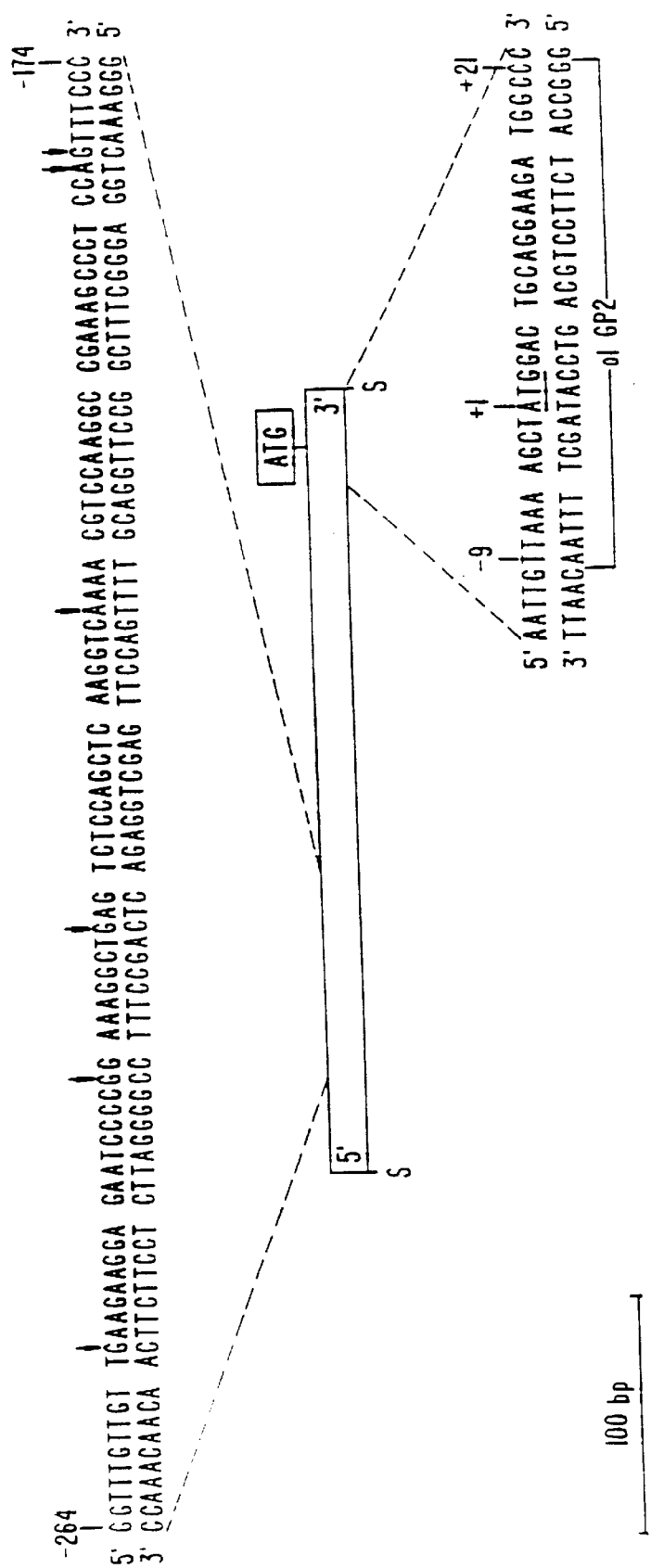

The primer extension assay, performed with ol GP2 (FIG. 4C) confirmed the five major products corresponding in length to the transcripts predicted by S1 analysis (FIG. 4B). It should be noted that other bands are seen in primer extension experiments probably due to both minor RNA species and early termination of the reverse transcriptase reaction.

EXAMPLE 3

Chromosome Mapping with Somatic Cell Hybrid Panel

A chromosome mapping panel was used to assign the CR-1 gene to human chromosomes. A 1.5 kb long PstI fragment derived from CR-1 (CR-1-P3, FIG. 3 top) was used to probe a Southern blot of TaqI-digested genomic DNAs prepared from 23 hamster human somatic cell hybrids (Table I). Under conditions of high stringency one human specific genomic fragment of 4.5 kb hybridized to the probe. The presence of the 4.5 kb fragment could be clearly distinguished in the DNA of the hybrid cell lines containing chromosome 3 (Table I).

Figures 5A, 5B:
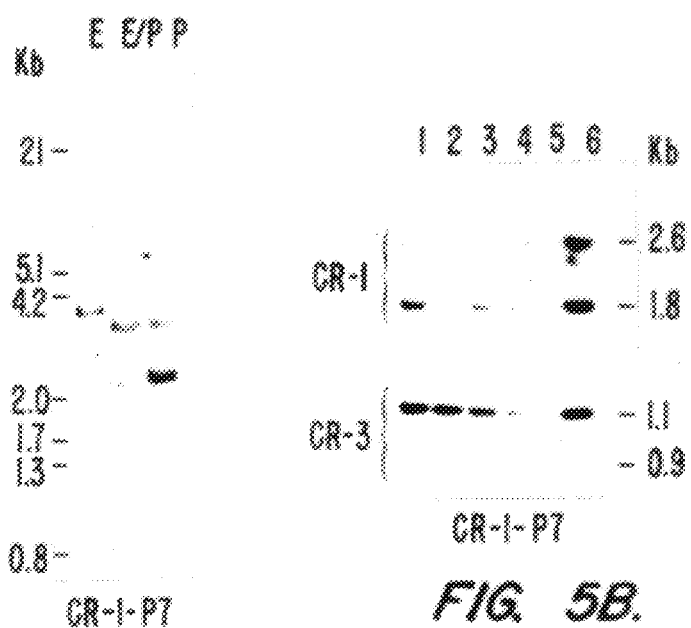
FIGS. 5A and 5B. Southern blot analysis using the CR-1-P7 probe.

When the EcoRI-PstI fragment (CR-1-P7) containing 800 bp upstream of the translation initiation (see FIG. 3 top) was used to probe the same Southern blot described previously and shown in FIG. 1, hybridization to two fragments was seen (e.g., in the lane containing human DNA digested with EcoRI and PstI (FIG. 5A), the 0.8 kb band corresponds to the genomic sequence CR-1). This indicated that the 5' region of the CR-1 gene was present in two copies in the human genome. When the CR-1-P7 fragment was used to probe the above-mentioned hamster-human somatic cell hybrid panel, it was possible to obtain the segregation of the two sequences (FIG. 5B). Because of the hybridization pattern summarized in Table I and, in particular, the pattern obtained using the hybrid cell lines containing portions of the X chromosome already described (Rocchi et al. 1986), the second genomic copy can be assigned to the Xq21–22 region.

TABLE 1

Segregation of CRIPTO-related sequences in human/hamster hybrids

| Cell lines | Chromosomes present | CR-1 | CR-3 |
| --- | --- | --- | --- |
| HY.19.16T30 | Xq−, 10, 12, 13, 14, 15, 18, 20 | − | − |
| HY.22AZA1 | t(X; X)[a], 5, 12, 14, 17, 18, 19 | − | + |
| HY.31.24E | X, 5, 8, 11, 12, 14, 21 | − | + |
| HY.36.1 | X, 8, 11, 19 | − | + |
| HY.60A | X, 5, 6, 8, 13, 14, 18, 20 | − | + |
| HY.70B1A | t(X; 21)[b], 6, 15, 16 | − | − |
| HY.70B2 | t(X; 21)[b], 6, 13, 15, 16 | − | − |
| HY.75E1 | X, 5, 9, 12 | − | + |
| HY.94A | X, 6, 7, 8, 16, 22 | − | + |
| HY.94BT1 | t(X; Y)[c], 4, 7, 9, 11, 12, 20 | − | + |
| HY.95A1 | X, 3, 5, 10, 11, 14 | + | + |
| HY.95B | X, 4, 6, 7, 14, 18, 22 | − | + |
| HY.95S | X, 2, 3, 13, 21 | + | + |
| HY.112F7 | t(X; 11)[d], 3, 4, 8, 10, 20 | + | + |
| RJ.369.1T2 | 13, 22 | − | − |
| Y.173.5CT3 | Xi, 1, 3, 4, 6, 8, 11, 12, 14, 15, 18, 21, 22 | + | + |
| YC2T1 | X, 1, 11, 12, 14, 18, 19, 20 | − | + |
| HY.136C | X | − | + |
| Y.X6.8B2 | t(X; 6)[e], 1, 3, 5, 12, 13, 14, 15, 17, 21, 22 | + | + |
| Y.162AZA | t(X; hamster)[f] | − | + |
| HY.87Z4 | t(X; 11)[g], 1, 2, 4, 5, 6, 12, 15, 20 | − | − |

TABLE 1-continued

Segregation of CRIPTO-related sequences in human/hamster hybrids

| Cell lines | Chromosomes present | CR-1 | CR-3 |
|---|---|---|---|
| HY.85D30T2 | t(X; 1)[h], 2, 3, 8, 11, 13, 18, 21 | + | + |
| HY.84T2 | Y | − | − |
| Chromosome assignment | | 3 | Xq21–Xq22 |
| Number concordant + | | 6 | 17 |
| Number concordant − | | 17 | 6 |
| Number discordant | | 0 | 0 |

Note:
+ and − indicate, respectively, presence or absence of CR-1 and CR-3 sequences
[a]Xqter → Xq21::Xp22.3 → Xqter
[b]Xqter → Xq22::21p13 → 21qter
[c]Xqter → Xp22.3::Yp → Yqter
[d]Xqter → Xq11.1::11p11.2 → 11q11
[e]Xqter → Xq21.3::6q27 → 6pter
[f]Xpter → Xq27.3::hamster
[g]Xqter → Xq26::11q23 → 11pter

EXAMPLE 4

Isolation and Characterization of a Second Genomic CRIPTO-Related Sequence

A genomic library was screened to isolate the genomic clones containing the 5' cDNA non-coding region using as probe the labeled CR-1-P7 DNA fragment (FIG. 3). Only two different classes of recombinant phages were found exhibiting the restriction pattern expected from the Southern blot (FIGS. 5A and 5B).

The restriction map of clone CR-3 is shown in FIG. 3 bottom. To investigate whether the CRIPTO related genomic sequences from recombinant lambda CR-3 clones encode a complete CRIPTO protein, the nucleotide sequence of a 2688 bp fragment hybridizing to 2B3 and G2 was determined and compared this sequence with that of cDNA (FIGS. 2 and 3 bottom).

Analysis of the nucleotide sequence of CR-3 revealed that this clone includes a complete CRIPTO cDNA lacking introns and containing a poly(A) tract at the 3' end. Seven single base pair substitutions are observed in the coding region (FIG. 2) and six of these give rise to amino acid changes. THe 3' non-coding sequence is less similar (97% identical) to CR-1. Most of the base changes, deletions and insertions fall within the inverted Alu sequence. The unusual polyA addition site AGTAAA present in the CR-1 gene is conserved also in CR-3. The similarity between CR-1 and CR-3 extends for 697 nucleotides upstream of the initiator AUG where it is possible to observe 7 base pair substitutions and 6 nucleotide deletions.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AATTGTTAAA GCTATGGACT GCAGGAAGAT GGCCC                                    35
```

( 2 ) INFORMATION FOR SEQ ID NO:2:

( i ) SEQUENCE CHARACTERISTICS:
        ( A ) LENGTH: 5761 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(887..921, 2011..2063, 2147..2281,
                2652..2766, 2865..2974, 4049..4167)

( x i ) SEQUENCE DESCRIPTION: SEQ ID NO:2:

```
GCCGGCACTC CCACTGGAGA GTCCCAGCTG CCTCTGGCCG CCCCTCCCCT CTCCCGGGCA      60
CCTGGCGCCG CTCCCGCGTC CTTTCAGGAA TTCACGTCCG CCTGGAATTT GCACTTCAAG     120
TCTGGAGCCC CCAAGGAACC CCTCCTGACC CTGAACTTCT ATCTCAGTTT CAAGCTTCCT     180
AGTCTTCCCC ACACACACAC ACCTAGCTCC TCAGGCGGAG AGCACCCCTT TCTTGGCCAC     240
CCGGGTATCC CCCAGGGAGT ACGGGGCTCA AAACACCCTT CTGGAAAAAA CAAAGGTGGA     300
AGCAAATTTC AGGAAGTAAA ACTTCTGAAA TAAAATAAAA TATCGAATGC CTTGAGACCC     360
ATACATTTTC AGGTTTTCCT AATTAAAGCA ATTACTTTCC ACCACCCCTC CAACCTGGAA     420
TCACCAACTT GATTAGAGAA ACTGATTTTT CTTTTTTCTT TTTTTTTCCC GAAAAGAGTA     480
CCTCTGATCA TTTTAGCCTG CAACTAATGA TAGAGATATT AGGGCTAGTT AACCACAGTT     540
TTACAAGACT CCTCTTCCCG CGTGTGGGCC ATTGTCATGC TGTCGGTCCC GCCCACCTGA     600
AAGGTCTCCC CGCCCCGACT GGGGTTTGTT GTTGAAGAAG GAGAATCCCC GGAAAGGCTG     660
AGTCTCCAGC TCAAGGTCAA AACGTCCAAG GCCGAAAGCC CTCCAGTTTC CCCTGGACGC     720
CTTGCTCCTG CTTCTGCTAC GACCTTCTGG GGAAAACGAA TTTCTCATTT TCTTCTTAAA     780
TTGCCATTTT CGCTTTAGGA GATGAATGTT TTCCTTTGGC TGTTTTGGCA ATGACTCTGA     840
ATTAAAGCGA TGCTAACGCC TCTTTTCCCC CTAATTGTTA AAAGCT ATG GAC TGC        895
                                                  Met Asp Cys
                                                   1
AGG AAG ATG GCC CGC TTC TCT TAC AG  GTATGAGCTA ATCTTAGAAT             941
Arg Lys Met Ala Arg Phe Ser Tyr Ser
    5                   10
AGTGAACTTT TTTTGATTGC TAGAGATTGC CAGCTTAGGA AGTAATGTTC TACACTGTCA    1001
TTTGATTTTT CTCCTTGCTC AAGCCTTAAA AGAGCTGCCA ACCGACTGCT GTTTTCCTG     1061
AAAGACCTGG AATTTCACAT GGTTACTTCT AACTTTGCCA TTGGCTTTTA ACATTTTCGT    1121
GTTAATGTTA ATTTTCATTT TATGTTAATG ACTCTGCCTA TGAAATAGTG TTTCTTTACT    1181
TCTTGTACAA ATAAAGGTCA GTACTACAAC CAAATTTAAA TCTTCCGAAA AGATTAAAGG    1241
TATAAGCAGA TTCAATACTT GGCAAAACTA TTAAGATAAT AGCAAAAAAA AAAAAAAAAC    1301
CCACATTTTT TACCTAAAAA CCTTTTAAGT GATTGGTTAA AATAGTTTGG CCGGGTGCGG    1361
TGGCTCACGC CTGTAATCCT AGCACTTTGG GAGGCAGAGG CGGGTGGATC ACTGAGGTCA    1421
GGAGACCAGC CTGGCCAACA TGGCAAAACC CCGTCTCTAT TAAAAATACA AAAATTAGCC    1481
AAGCATGGTG GCGGGCACCT GTAATCCCAG CTACTCTGGA GGCTGAGGCA GGAGAATTGC    1541
TTGAACTGGG GAGGGGAGGC AGTGAGCCGA GATCGCACCA TTGCACTCCA GCCTGGGTGA    1601
AAAACCGAAA CTCCCTCTCA AAAATAAATA AATAAATACA GTAGTTTGTA AAATGATTCA    1661
TCGGTAACAT GGGATGCAGC TATTTTTTAA TCCTTATATG AAAATTGTAT GCAGGGGAAA    1721
ACATGTGAAA TAGAAGATAA AAGACATATA CCTACTTAAA ATTAGGTACT TATGTGAGGA    1781
CAGGGCCTAA GAAATAATAA TATATATTAA AAAGACTTGG ATATTGGTGA CTTTTTTTCA    1841
ACATTTTTCT TTGTTACATG AATTAGCCAT TAAAAAAAGA AAGATGGTGC TCTACAATTT    1901
CTTTTCAGTG ATCTGTGGTC TTGTCCTTGT GATGAGAGGA CCTGGGTGTT AACTTGTAAG    1961
GTTTTATTTC CTTTGTTTGG CTAACTCATG TTTGACTTCC TCTTCCTAG T GTG ATT      2017
                                                        Val Ile
TGG ATC ATG GCC ATT TCT AAA GTC TTT GAA CTG GGA TTA GTT GCC G        2063
Trp Ile Met Ala Ile Ser Lys Val Phe Glu Leu Gly Leu Val Ala
 15                   20                  25
GTGAGAGACC TTTTGTTTCT TTTGATCACT CTCAATTTTA TGTGGCCTAA AATACAGACT    2123
CCATGAATTG ATTTGTCGTT AAG  GG CTG GGC CAT CAG GAA TTT GCT CGT        2172
```

|                                                                                                          |      |
| -------------------------------------------------------------------------------------------------------- | ---- |
| Gly Leu Gly His Gln Glu Phe Ala Arg<br>30                          35                                    |      |
| CCA TCT CGG GGA TAC CTG GCC TTC AGA GAT GAC AGC ATT TGG CCC CAG<br>Pro Ser Arg Gly Tyr Leu Ala Phe Arg Asp Asp Ser Ile Trp Pro Gln<br>40                   45                      50 | 2220 |
| GAG GAG CCT GCA ATT CGG CCT CGG TCT TCC CAG CGT GTG CCG CCC ATG<br>Glu Glu Pro Ala Ile Arg Pro Arg Ser Ser Gln Arg Val Pro Pro Met<br>55                   60                      65                       70 | 2268 |
| GGG ATA CAG CAC A GTAAGAACTG CCTGACTTCG ATGCTTCTGC CCTGGCCCTT<br>Gly Ile Gln His | 2321 |
| CATGTGTCTC CTGACTATCT TTCCAACACT CTTTCACCTA AAAGGGCACC TGGTTCTGGA | 2381 |
| ACTGTGCAGG TGCTGGACTG CTTTGGTTTT GGAAGTGAGA CAAGGATTGT GTATTTTACT | 2441 |
| TCCCTAGAGT GCAGTTTCCT CCCCTGAGTC CACTTCACAC TGGGAACCCA GAACCACCAC | 2501 |
| TGGCCTATGC ATGAAAATGA CTTCTCTGCT CAAAGGCACA GAGTCTTACT CTGATACAAC | 2561 |
| ACATTGGTGT TGTATTAACC TTCGCTTACA GGAATTGCCC TTGCACTTTT CCATCCCTAC | 2621 |
| ACCTCAGTCA TTCTGTTCTT ACCTTTCAAG GT AAG GAG CTA AAC AGA ACC TGC<br>                                             Ser Lys Glu Leu Asn Arg Thr Cys<br>                                              75                      80 | 2674 |
| TGC CTG AAT GGG GGA ACC TGC ATG CTG GGG TCC TTT TGT GCC TGC CCT<br>Cys Leu Asn Gly Gly Thr Cys Met Leu Gly Ser Phe Cys Ala Cys Pro<br>85                    90                     95 | 2722 |
| CCC TCC TTC TAC GGA CGG AAC TGT GAG CAC GAT GTG CGC AAA GA<br>Pro Ser Phe Tyr Gly Arg Asn Cys Glu His Asp Val Arg Lys Glu<br>100                  105                  110 | 2766 |
| GTAAGCAATT CAGAGGGGCG GGGAGCCGTG GAGAGGAGAG AGAAAGGGAA GTGGAAATTT | 2826 |
| CAGACCCAAG CTATCGCAGC TTACCTGTTC ATTCTCAG G AAC TGT GGG TCT GTG<br>                                                       Asn Cys Gly Ser Val<br>                                                                 115 | 2880 |
| CCC CAT GAC ACC TGG CTG CCC AAG AAG TGT TCC CTG TGT AAA TGC TGG<br>Pro His Asp Thr Trp Leu Pro Lys Lys Cys Ser Leu Cys Lys Cys Trp<br>120                  125                  130 | 2928 |
| CAC GGT CAG CTC CGC TGC TTT CCT CAG GCA TTT CTA CCC GGC TGT G<br>His Gly Gln Leu Arg Cys Phe Pro Gln Ala Phe Leu Pro Gly Cys<br>135                  140                  145 | 2974 |
| GTAAGCGGAG GTTCTCCTCT TTCTTTTGCC CTTTGAAGTT ACGTAGTTGC CTTGGGGGGT | 3034 |
| GCTTAGTTAG CAGGCTCTCC TTGTACCTCT TGTCTTGCTA GAGCCTGGCA GCCAAAGTTC | 3094 |
| TGCTTATAAA AGCATCGCAG ACTCCTGATG AGATAGTTGC CTTGGCCTCT TTGATATTTA | 3154 |
| TTTCCTCGGG AACCTGGCTA GTCCTGCTGC CTTTCAGATA GAGATGTATT TCAAGTCTAT | 3214 |
| TTGACATTTT ATGGTCTGAA CTTCTATTGA GGAAATAAA CAAGTCTCGG TCTCTTGTTA | 3274 |
| AACCAAGAGA TGTTCTCTGG TGTTCCTTTC CTTTGGGTAG GGGGGACCCA AACCAGGATG | 3334 |
| GGCAGCTCAT TTAGAGCCCA CCCTGACGAC AAATTCTATC AGAGGCTTGG CCCCTTGCTA | 3394 |
| GTCCTTTAGA AACTTCCAGA GTCCTAAAAG TCCCTGGTAA CCCCCTCCCC ATACCTTACC | 3454 |
| ATGACTGGTC ACAGAACCCT TACCATGACT GGTCACAGAA CCCTTTCACC TTCTTGATTT | 3514 |
| TTTACTGATT TGAGGAATAC AATGAAAAGA AGGGCAGCAC CTGGAGAGGA AAAGAGGCGA | 3574 |
| CAGTCCTCTC TCCACCCTAG CCTGAGCCAG GTTTCTAGGG CCCCCCAAAT TCAGAGACCT | 3634 |
| ATTATAGTTC TGGGCCTTGG AGATGTAGAA ATGGAAAATA TTCAAGCCCA GGAAGTAAAT | 3694 |
| GAAAGCAAAC ATTTCACTGA GAACAGGAAG GAATTCCCCA ATCCAGACAG GGATTGTGTC | 3754 |
| TTTGCCATTT GCATCCTGGG TGTCAGGCTC AGGATAGGTG TTTGATAAGT GTGGGTTGGG | 3814 |
| TGATTGGATG TGTAGGGAAC ATTTGCTCTT CCTGGAACAT GGGGCCCAAG TCAGAATCTA | 3874 |

```
ACCCAGGTTG  TGCTCATTCC  TGCAAGTGAA  GGCATCACCA  CTGGGCTAGG  TTCCAGGTGT      3934

GAGTGTCCTG  AGAAGAGCAG  GTTCACAGTA  GCGTATAGAT  ATGCCACATT  TGTGGGCAGC      3994

AGGATGAACT  GCCAGAGAGG  TTTGCTTTAA  TGACCAAGCA  TCCCTACCTT  CCAG      AT    4050
                                                                     Asp
                                                                     150

GGC  CTT  GTG  ATG  GAT  GAG  CAC  CTC  GTG  GCT  TCC  AGG  ACT  CCA  GAA  CTA      4098
Gly  Leu  Val  Met  Asp  Glu  His  Leu  Val  Ala  Ser  Arg  Thr  Pro  Glu  Leu
                    155                     160                     165

CCA  CCG  TCT  GCA  CGT  ACT  ACC  ACT  TTT  ATG  CTA  GTT  GGC  ATC  TGC  CTT      4146
Pro  Pro  Ser  Ala  Arg  Thr  Thr  Thr  Phe  Met  Leu  Val  Gly  Ile  Cys  Leu
                    170                     175                     180

TCT  ATA  CAA  AGC  TAC  TAT  TAATCGACAT  TGACCTATTT  CCAGAAATAC                    4194
Ser  Ile  Gln  Ser  Tyr  Tyr
                    185

AATTTTAGAT  ATCATGCAAA  TTTCATGACC  AGTAAAGGCT  GCTGCTACAA  TGTCCTAACT      4254

GAAAGATGAT  CATTTGTAGT  TGCCTTAAAA  TAATGAATAC  AATTTCCAAA  ATGGTCTCTA      4314

ACATTTCCTT  ACAGAACTAC  TTCTTACTTC  TTTGCCCTGC  CCTCTCCCAA  AAAACTACTT      4374

CTTTTTTCAA  AAGAAAGTCA  GCCATATCTC  CATTGTGCCT  AAGTCCAGTG  TTTCTTTTTT      4434

TTTTTTTTTT  TGAGACGGAC  TCTCACTCTG  TCACCCAGGC  TGGACTGCAA  TGACGCGATC      4494

TTGGTTCACT  GCAACCTCCG  CATCCGGGGT  TCAAGCCATT  CTCCTGCCTA  AGCCTCCCAA      4554

GTAACTGGGA  TTACAGGCAT  GTGTCACCAT  GCCCAGCTAA  TTTTTTTGTA  TTTTTAGTAG      4614

AGATGGGGGT  TTCACCATAT  GGCCAGTCT  GGTCTCGAAC  TCCTGACCTT  GTGATCCACT       4674

CGCCTCAGCC  TCTCGAAGTG  CTGAGATTAC  ACACGTGAGC  AACTGTGCAA  GGCCTGGTGT      4734

TTCTTGATAC  ATGTAATTCT  ACCAAGGTCT  TCTTAATATG  TTCTTTAAA  TGATTGAATT       4794

ATATGTTCAG  ATTATTGGAG  ACTAATTCTA  ATGTGGACCT  TAGAATACAG  TTTTGAGTAG      4854

AGTTGATCAA  AATCAATTAA  AATAGTCTCT  TTAAAAGGAA  AGAAAACATC  TTTAAGGGA       4914

GGAACCAGAG  TGCTGAAGGA  ATGGAACTCC  ATCTCCGTGT  GTGCAGGGAG  ACTGGGTAGG     4974

AAAGAGGAAG  CAAATAGAAG  AGAGAGGTTG  AAAAACAAAA  TGGGTTACTT  GATTGGTGAT     5034

TAGGTGGTGG  TAGAGAAGCA  AGTAAAAAGG  CTAAATGGAA  GGGCAAGTTT  CCATCATCTA     5094

TAGAAAGCTA  TATAAGACAA  GAACTCCCCT  TTTTTTCCCA  AAGGCATTAT  AAAAAGAATG     5154

AAGCCTCCTT  AGAAAAAAAA  TTATACCTCA  ATGTCCCCAA  CAAGATTGCT  TAATAAATTG     5214

TGTTTCCTCC  AAGCTATTCA  ATTCTTTTAA  CTGTTGTAGA  AGACAAAATG  TTCACAATAT     5274

ATTTAGTTGT  AAACCAAGTG  ATCAAACTAC  ATATTGTAAA  GCCCATTTTT  AAAATACATT     5334

GTATATATGT  GTATGCACAG  TAAAAATGGA  AACTATATTG  ACCTAAATGT  GAACTGGTTA     5394

TTTCTAGGTG  GTGAGGTGCT  TTATGGTGGT  GGGTTTTGC  TCTTGATGCC  CTTTTTGCAT      5454

TTTCCAAAGT  ACCATGGTGA  GGATGTGTTA  TATCTTTTCC  AGGGTCCTAA  AAGTCCCTGG     5514

CAACTCCCTC  CCCATACCCT  ACCATGACTG  GTCACAGAAC  CCTTTCACCT  TATTGATTTG     5574

TACTGATTTC  ATATGGAATA  TGGCAACTAC  ATCTGGCTCA  AAACAAGGA  AACCAGAAGA      5634

GCCAAGTCCC  AGGTGAGTGC  TCAGTTCTGT  TTCTAGCTTT  GACGTGTGTG  TTCTTCTGTG     5694

AAGGACAAAA  TTTGCTTCTA  TTATTTAGGT  ACCATAATTT  GTGTTTTCC  AAATTAATTC      5754

CCTGCAG                                                                    5761
```

( 2 ) INFORMATION FOR SEQ ID NO:3:

( i ) SEQUENCE CHARACTERISTICS:
    ( A ) LENGTH: 188 amino acids
    ( B ) TYPE: amino acid -continued ( D ) TOPOLOGY: linear ( i i ) MOLECULE TYPE: protein ( x i ) SEQUENCE DESCRIPTION: SEQ ID NO:3:

```
Met  Asp  Cys  Arg  Lys  Met  Ala  Arg  Phe  Ser  Tyr  Ser  Val  Ile  Trp  Ile
 1                   5                        10                            15

Met  Ala  Ile  Ser  Lys  Val  Phe  Glu  Leu  Gly  Leu  Val  Ala  Gly  Leu  Gly
              20                        25                       30

His  Gln  Glu  Phe  Ala  Arg  Pro  Ser  Arg  Gly  Tyr  Leu  Ala  Phe  Arg  Asp
              35                        40                       45

Asp  Ser  Ile  Trp  Pro  Gln  Glu  Pro  Ala  Ile  Arg  Pro  Arg  Ser  Ser
         50                        55                       60

Gln  Arg  Val  Pro  Pro  Met  Gly  Ile  Gln  His  Ser  Lys  Glu  Leu  Asn  Arg
 65                       70                        75                           80

Thr  Cys  Cys  Leu  Asn  Gly  Gly  Thr  Cys  Met  Leu  Gly  Ser  Phe  Cys  Ala
                    85                        90                       95

Cys  Pro  Pro  Ser  Phe  Tyr  Gly  Arg  Asn  Cys  Glu  His  Asp  Val  Arg  Lys
              100                       105                      110

Glu  Asn  Cys  Gly  Ser  Val  Pro  His  Asp  Thr  Trp  Leu  Pro  Lys  Lys  Cys
              115                       120                      125

Ser  Leu  Cys  Lys  Cys  Trp  His  Gly  Gln  Leu  Arg  Cys  Phe  Pro  Gln  Ala
     130                       135                       140

Phe  Leu  Pro  Gly  Cys  Asp  Gly  Leu  Val  Met  Asp  Glu  His  Leu  Val  Ala
145                       150                       155                      160

Ser  Arg  Thr  Pro  Glu  Leu  Pro  Pro  Ser  Ala  Arg  Thr  Thr  Thr  Phe  Met
                    165                       170                      175

Leu  Val  Gly  Ile  Cys  Leu  Ser  Ile  Gln  Ser  Tyr  Tyr
              180                       185
```

( 2 ) INFORMATION FOR SEQ ID NO:4:

( i ) SEQUENCE CHARACTERISTICS:
       ( A ) LENGTH: 2675 base pairs
       ( B ) TYPE: nucleic acid
       ( C ) STRANDEDNESS: double
       ( D ) TOPOLOGY: linear ( i i ) MOLECULE TYPE: DNA (genomic)

( i x ) FEATURE:
       ( A ) NAME/KEY: CDS
       ( B ) LOCATION: 809..1372

( x i ) SEQUENCE DESCRIPTION: SEQ ID NO:4:

```
AAGCTTGCGC  GCCATGTAAG  GTAAAGTGAC  TGATTCTATA  GCAATCCAAT  TGTTCCTTTG     60

TCTGCCCGTT  TACATATAAC  AATGTTGTCA  ATGTTTGATT  GAAAATACCT  AGCAGGTGAC    120

ACACACACAC  CTAGCTCCTC  AGGCGGAGAG  CACCCCTTTC  TTGGCCACCC  GGGTATCCCC    180

CAGGGAGTAC  GGGGCTCAAA  ACACCCTTTT  GGAGAACAAG  GTGGAAGCAA  ATTTCAGGAA    240

GTAAAACTTC  CGAAATAAAA  TAAATATCG   AATGCCTTGA  GACCCATACA  TTTTCAGGTT    300

TTCCTAATTA  AAGCAATTAC  TTTCCACCAC  CCCTCCAACC  TGGAATCACC  AACTTGGTTA    360

GAGAAACTGA  TTTTTCTTTT  TTCTTTTTTT  TTCCCAAAAG  AGTACATCTG  ATCATTTTAG    420

CCTGCAACTA  ATGATAGAGA  TATTAGGGCT  AGTTAACCAC  AGTTTTACAA  GACTCCTCTC    480

CCGCGTGTGG  GCCATTGTCA  TGCTGTCGGT  CCCGCCCACC  TGAAAGGTCT  CCCCGCCCCG    540

ACTGGGGTTT  GTTGTTGAAG  AAGGAGAATC  CCCGGAAAGG  CTGAGTCTCC  AGCTCAAGGT    600

CAAAACGTCC  AAGGCCGAAA  GCCCTCCAGT  TTCCCCTGGA  CACCTTGCTC  CTGCTTCTGC    660
```

```
TACGACCTTC TGGGAACGCG AATTTCTCAT TTTCTTCTTA AATTGCCATT TTCGCTTTAG    720

GAGATGAATG TTTTCCTTTG GCTGTTTTGG CAATGACTCT GAATTAAAGC GATGCTAACG    780

CCTCTTTTCC CCCTAATTGT TAAAAGCT ATG GAC TGC AGG AAG ATG GTC CGC      832
                              Met Asp Cys Arg Lys Met Val Arg
                              190                     195

TTC TCT TAC AGT GTG ATT TGG ATC ATG GCC ATT TCT AAA GCC TTT GAA     880
Phe Ser Tyr Ser Val Ile Trp Ile Met Ala Ile Ser Lys Ala Phe Glu
            200             205             210

CTG GGA TTA GTT GCC GGG CTG GGC CAT CAA GAA TTT GCT CGT CCA TCT     928
Leu Gly Leu Val Ala Gly Leu Gly His Gln Glu Phe Ala Arg Pro Ser
            215             220             225

CGG GGA GAC CTG GCC TTC AGA GAT GAC AGC ATT TGG CCC CAG GAG GAG     976
Arg Gly Asp Leu Ala Phe Arg Asp Asp Ser Ile Trp Pro Gln Glu Glu
230             235             240

CCT GCA ATT CGG CCT CGG TCT TCC CAG CGT GTG CTG CCC ATG GGA ATA    1024
Pro Ala Ile Arg Pro Arg Ser Ser Gln Arg Val Leu Pro Met Gly Ile
245             250             255             260

CAG CAC AGT AAG GAG CTA AAC AGA ACC TGC TGC CTG AAT GAG GGA ACC    1072
Gln His Ser Lys Glu Leu Asn Arg Thr Cys Cys Leu Asn Glu Gly Thr
                265             270             275

TGC ATG CTG GGG TCC TTT TGT GCC TGC CCT CCC TCC TTC TAC GGA CGG    1120
Cys Met Leu Gly Ser Phe Cys Ala Cys Pro Pro Ser Phe Tyr Gly Arg
            280             285             290

AAC TGT GAG CAC GAT GTG CGC AAA GAG AAC TGT GGG TCT GTG CCC CAT    1168
Asn Cys Glu His Asp Val Arg Lys Glu Asn Cys Gly Ser Val Pro His
        295             300             305

GAC ACC TGG CTG CCC AAG AAG TGT TCC CTG TGT AAA TGC TGG CAC GGT    1216
Asp Thr Trp Leu Pro Lys Lys Cys Ser Leu Cys Lys Cys Trp His Gly
310             315             320

CAG CTC CGC TGC TTT CCT CAG GCA TTT CTA CCC GGC TGT GAT GGC CTT    1264
Gln Leu Arg Cys Phe Pro Gln Ala Phe Leu Pro Gly Cys Asp Gly Leu
325             330             335             340

GTG ATG GAT GAG CAC CTC GTG GCT TCC AGG ACT CCA GAA CTA CCA CCG    1312
Val Met Asp Glu His Leu Val Ala Ser Arg Thr Pro Glu Leu Pro Pro
            345             350             355

TCT GCA CGT ACT ACC ACT TTT ATG CTA GCT GGC ATC TGC CTT TCT ATA    1360
Ser Ala Arg Thr Thr Thr Phe Met Leu Ala Gly Ile Cys Leu Ser Ile
            360             365             370

CAA AGC TAC TAT TAATCGACAT TGACCTATTT CCAGAAATAC AATTTTAGAT        1412
Gln Ser Tyr Tyr
        375

ATTATGCAAA TTTCATGACC CGTAAAGGCT GCTGCTACAA TGTCCTAACT GAAAGATGAT  1472

CATTTGTAGT TGCCTTAAAA TAATGAATAC AATTTCCAAA ACGGTCTCTA ACATTTCCTT  1532

ACAGAACTAA CTACTTCTTA CCTCTTTGCC CTGCCCTCTC CCAAAAAACT ACTTCTTTTT  1592

TCAAAGAAA GTCAGCCATA TCTCCATTGT GCCCAAGTCC AGTGTTTCTT TTTTTTTTT    1652

GAGACGGACT CTCACTCTGT CACCCAGGCT GGACTGCAAT GACGCGATCT TGGTTCACCG  1712

CAACCTCCGC ATCCGGGGTT CAAGCCATTC TCCTGCCTCA GCCTCCCAAG TAGCTGGGAT  1772

TACAGGCATG TGTCACCATG CCGGCTAATT TTTTTGTATT TTTAGTAGAG ACGGGGTTT   1832

CACCATATTG GCCAGTCTGG TCTCGAACTC TGACCTTGTG ATCCATCGCT CGCCTCTCAA  1892

GTGCTGAGAT TACACACGTG AGCAACTGTG CAAGGCCTGG TGTTTCTTGA TACATGTAAT  1952

TCTACCAAGG TCTTCTTAAT ATGTTCTTTT AAATGATTGA ATTATACACT CAGATTATTG  2012

GAGACTAAGT CTAATGTGGA CCTTAGAATA CAGTTTTGAG TAGAGTTGAT CAAAATCAAT  2072

TAAAATAGTC TCTTTAAAAG GAAAGAAAAC ATCTTTAAGG GGAGGAACCA GAGTGCTGAA  2132
```

```
GGAATGGAAC  TCCATCTCCG  TGTGTGCAGG  GAGACTGGGT  AGGAAAGAGG  AAGCAAATAG    2192

AAGAGAGG    TTGAAAAACA  AAATGGGTTA  CTTGATTGGT  GATTAGGTGG  TGGTAGAGAA    2252

GCAAGTAAAA  AGGCTAAATG  GAAGGGCAAG  TTTCCATCAT  CTATAGAAAG  CTATGTAAGA    2312

CAAGGACTCC  CCTTTTTTTC  CCAAAGGCAT  TGTAAAAGA   ATGAAGTCTC  CTTAGAAAAA    2372

AAATTATACC  TCAATGTCCC  CAACAAGATT  GCTAATAAA   TTGTGTTTCC  TCCAAGCTAT    2432

TCAATTCTTT  TAACTGTTGT  AGAAGAGAAA  ATGTTCACAA  TATATTTAGT  TGTAAACCAA    2492

GTGATCAAAC  TACATATTGT  AAAGCCCATT  TTTAAAATAC  ATTGTATATA  TGTGTATGCA    2552

CAGTAAAAAT  GGAAACTATA  TTGACCTAAA  AAAAAAAAA   GGAAACCACC  CTTAGGCAGG    2612

CAGGACATGC  TCTTCAGAAC  TCTGCTCTTC  AGAGTTCCAA  AGAAGGGATA  AACATCTTT     2672

TAT                                                                       2675
```

( 2 ) INFORMATION FOR SEQ ID NO:5:

( i ) SEQUENCE CHARACTERISTICS:
        ( A ) LENGTH: 188 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Asp  Cys  Arg  Lys  Met  Val  Arg  Phe  Ser  Tyr  Ser  Val  Ile  Trp  Ile
 1              5                        10                       15

Met  Ala  Ile  Ser  Lys  Ala  Phe  Glu  Leu  Gly  Leu  Val  Ala  Gly  Leu  Gly
               20                       25                  30

His  Gln  Glu  Phe  Ala  Arg  Pro  Ser  Arg  Gly  Asp  Leu  Ala  Phe  Arg  Asp
          35                       40                       45

Asp  Ser  Ile  Trp  Pro  Gln  Glu  Glu  Pro  Ala  Ile  Arg  Pro  Arg  Ser  Ser
     50                        55                       60

Gln  Arg  Val  Leu  Pro  Met  Gly  Ile  Gln  His  Ser  Lys  Glu  Leu  Asn  Arg
 65                      70                       75                       80

Thr  Cys  Cys  Leu  Asn  Glu  Gly  Thr  Cys  Met  Leu  Gly  Ser  Phe  Cys  Ala
                    85                       90                       95

Cys  Pro  Pro  Ser  Phe  Tyr  Gly  Arg  Asn  Cys  Glu  His  Asp  Val  Arg  Lys
               100                      105                      110

Glu  Asn  Cys  Gly  Ser  Val  Pro  His  Asp  Thr  Trp  Leu  Pro  Lys  Lys  Cys
          115                      120                      125

Ser  Leu  Cys  Lys  Cys  Trp  His  Gly  Gln  Leu  Arg  Cys  Phe  Pro  Gln  Ala
     130                      135                      140

Phe  Leu  Pro  Gly  Cys  Asp  Gly  Leu  Val  Met  Asp  Glu  His  Leu  Val  Ala
145                      150                      155                      160

Ser  Arg  Thr  Pro  Glu  Leu  Pro  Pro  Ser  Ala  Arg  Thr  Thr  Thr  Phe  Met
                    165                      170                      175

Leu  Ala  Gly  Ile  Cys  Leu  Ser  Ile  Gln  Ser  Tyr  Tyr
               180                      185
```

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

-continued ( x i ) SEQUENCE DESCRIPTION: SEQ ID NO:6:

CCCGGTAGAA GGACGTCAGG TATCGAAATT GTTAA    35

What is claimed is:

1. An antibody having binding affinity to a human CRIPTO-related polypeptide-3 (CR-3) and not to CR-1, wherein said CR-3 has the amino acid sequence set forth in SEQ ID NO:5.

2. The antibody according to claim 1, which is a monoclonal antibody.

* * * * *